United States Patent [19]

Flam

[11] Patent Number: 5,181,905
[45] Date of Patent: Jan. 26, 1993

[54] METHOD OF MONITORING THE CONDITION OF THE SKIN OR WOUND

[76] Inventor: Eric Flam, 29 Ainsworth Ave., East Brunswick, N.J. 08816

[21] Appl. No.: 759,129

[22] Filed: Sep. 10, 1991

Related U.S. Application Data

[63] Continuation of Ser. No. 446,341, Nov. 28, 1989, abandoned.

[51] Int. Cl.⁵ .................. A61F 13/00; A61F 15/00
[52] U.S. Cl. ..................... 602/41; 128/637; 128/736; 604/361; 374/161; 374/162
[58] Field of Search ............... 128/155, 156, 637, 736; 604/361; 374/161, 162; 602/41

[56] References Cited

U.S. PATENT DOCUMENTS

| | | | |
|---|---|---|---|
| 2,579,738 | 12/1951 | Hargreaves | 374/162 |
| 3,339,546 | 9/1967 | Chen | 128/156 |
| 3,661,142 | 5/1972 | Flam | 128/2 H |
| 3,972,328 | 8/1976 | Chen | 128/156 |
| 4,070,912 | 1/1978 | McNaughton et al. | 128/736 |
| 4,192,785 | 3/1980 | Chen et al. | 128/283 |
| 4,393,080 | 7/1983 | Pawelchak et al. | 428/355 |
| 4,538,546 | 4/1986 | Garde | 604/361 |
| 4,538,603 | 9/1985 | Pawelchak et al. | 128/156 |
| 4,551,490 | 11/1985 | Doyle et al. | 524/22 |
| 4,651,749 | 3/1987 | Sagi | 128/736 |
| 4,684,558 | 8/1987 | Keusch et al. | 428/40 |
| 4,738,674 | 4/1988 | Todd et al. | 604/361 |
| 4,813,942 | 3/1989 | Alvarez | 604/290 |

OTHER PUBLICATIONS

VII-C's, Liquid Crystal Brochure, pp. 1-8, 1987.
Chameleon "Brand of Encapsulated Liquid Crystals" Brochure pp. 1-15, (1973).
Seven C's, E-Z Temp Brochure.
Shea, "Pressure Sores-Classification and Management", Clinical Orthopaedics and Related Research, No. 12, Oct., 1975, 89-100.
Confortt, "Pressure Sores-Dressed For A Successful Healing" Nursing 89, pp. 58-61, (Mar. 1989).
Belcaro et al., "Encapsulated Liquid Crystal Thermography In Peripheral Arterial Disease", Acta Chir. Belg. 1983, pp. 430-435, (Nov. 1983).
Nilsson et al., "Leg Temperature Profiles . . . " Scand. J. Clin. Lab. Invest., vol. 39, 1979, pp. 171-177.
Mahanty et al. "Thermal Response Of Paraplegic Skin to the Application Of Localized Pressure", Arch. Phys. Med. Rehab., vol. 62, 608-611 (1981).
Mahanty et al., "Thermal Response Of Skin To Application of Localized Pressure", Arch. Phys. Med. Rehab. vol. 60, 584-589 (1979).
Newman et al., "Thermography As A Predictor of Sacral Pressure Sores," Age and Aging, vol. 10, pp. 14-18, 1981.
Trandel et al., "Thermographical Investigation of Decubitus Ulcers", Bulletin of Prosthetics Research, Fall 1975, pp. 137-153.
Rogers et al., "Preventing Recurrent Tissue Breakdowns After Pressure Sore Closures", Plastic & Reconstructive Surgery, Oct. 1975, 419-422.
Hahn et al., "Phase III Final Report Thermographic Studies of Tissue Trauma and Seating", Department of National Health & Welfare, Canada, 1-312, 1984.

*Primary Examiner*—Paul Prebilic
*Attorney, Agent, or Firm*—Richard H. Brink

[57] ABSTRACT

A dressing having a skin or wound contacting surface is provided with an indicator means on the opposite surface. The indicator means is capable of sensing the condition of the skin or wound underlying the dressing and conveying the information to the health care professional eliminating the need to frequently change the dressing.

3 Claims, 2 Drawing Sheets

METHOD OF MONITORING THE CONDITION OF THE SKIN OR WOUND

This is a continuation application of application Ser. No. 07/446,341 filed Nov. 28, 1989 now abandoned.

BACKGROUND OF THE INVENTION

The prevention and treatment of decubitus ulcers is an important aspect of health care. Patients who are comatose, diabetic, paraplegic or otherwise suffering from serious impairment of the neural and vascular systems are at risk of developing these pressure sores. Once the ulcer has progressed beyond the initial indications, treatment is difficult, long, and costly.

Studies have indicated correlations between thermal characteristics of skin and potential decubiti formation. These appear to be related to both increased temperatures and decreased blood flows to potential ulcer forming areas in compromised patients.

When an area of skin is compressed for a period of time the normal blood flow to the region is reduced. The amount of reduction depends on the applied pressure. The reaction of the tissues is a function of the pressure intensity, time of application and frequency of application. Under normal conditions, these factors produce a reaction of involuntary motion which tends to relieve the pressure from the affected region and redistribute it to another skin location. These motions occur with sufficient frequency so that no permanent tissue damage results. When the pressure is relieved, a hyperemic response occurs as the body seeks to compensate for the oxygen deprivation and metabolite accumulation by an increased blood flow. This response normally subsides in a few minutes as the tissues are restored to normal function. A component of this increased blood flow is a change in skin temperature during the response. Studies have shown that there is a pressure and time relationship for these events, and that the greater the applied pressure, the shorter the time interval of application must be if the effects are to be reversible.

SUMMARY OF THE INVENTION

This invention in its broadest aspects relates to a dressing incorporating an indicator. The indicator conveys to the health care professional information about the condition of the patient's skin or wound beneath the dressing. The indicator eliminates the need for removing the dressing and having the health care professional perform a visual or other examination of the skin or wound. As a result, decisions about the course of treatment can be made in a faster and more cost effective manner.

DETAILED DESCRIPTION OF THE INVENTION

Figure 1:
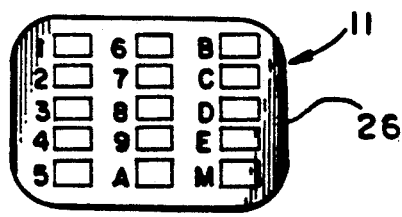
FIG. 1 is a top view of an encapsulated temperature sensitive liquid crystal tape.

This invention is directed to dressing type products having one surface which contacts the skin or overlies a wound and an indicator incorporated within or at another surface of the dressing. The indicator conveys information to the health care professional about the condition of the underlying skin or wound.

The dressing can be any of a number of different types constructed from various materials. Examples include gauze pads having a number of plys, non-adhesive gel type dressings such as the polyethylene oxide hydrogel disclosed by Keusch et al. in U.S. Pat. No. 4,684,558, adhesive gel-type products such as Elastogel, fluid interactive hydrocolloid dressings capable of adhering to both dry and moist skin surfaces such as those described by Chen in U.S. Pat. No. 3,339,546, by Chen et al. in U.S. Pat. No. 4,192,785, by Pawelchak et al. in U.S. Pat. No. 4,393,080, and by Doyle et al. in U.S. Pat. No. 4,551,490, and such hydrocolloid dressings including a polymeric foam layer for added flexibility and cushioning as described by Chen in U.S. Pat. No. 3,972,328 and by Pawelchak et al. in U.S. Pat. No. 4,538,603. The important criteria is that the dressing utilized transfers to the indicator information about the underlying skin or wound in an accurate and consistent manner.

The indicator is a means or substance that can visually inform the health care professional about the condition underlying the dressing. Examples of indicators that can be employed include pH sensitive solutions or papers which change color over a predetermined pH range and thus would show a change in the wound milieu by a change in color. Such solutions include bromcresol green at a pH range of 4.0 to 5.6, chlorphenol red at a pH of 5.2 to 6.8, bromthymol blue at a pH range of 6.0 to 7.6, phenyl red at a pH range of 6.8 to 8.4, and thymol blue at a pH range of 8.0 to 9.6, and such papers include universal and intermediate test papers sold under the tradenames ColorpHast ® (available from EM) and pH Hydrion Papers ® (available from Hydrion) and lithmus paper. Microbiological reagents that change color in the presence of certain microorganisms could be incorporated into the dressing to show a change in wound milieu by a change in color. Such microbiological reagents include an oxidase disc which undergoes pink-red-black color change as a positive indication of genus Neisseria bacteria available from Raven Biological (B1070), an indole reagent used to differentiate organisms that produce the enzyme tryptophanase which reacts with the amino acid tryptophane to produce indole available from Marion Scientific (261185), ferric chloride reagent which differentiates organisms capable of deamination of the amino acid phenylalanine available from Marion Scientific (261190), and nitrocefin reagent disc which is a sensitive beta-lactamase detector which produces a yellow-to-red color change available from BBL (Cefinase TM Reagent Disc 31626). Moisture indicators such as cobalt chloride which changes from blue to pink in the presence of moisture and from pink to blue when dry and could be incorporated into the dressing to show a change in the wound milieu by a change in color. A conducting indicator such as an electrochemical cell that becomes activated by moisture could be incorporated into the dressing to show a change in the wound milieu by a signal such as light or sound. Pressure indicators such as piezoelectric or piezoresistive elements could be incorporated into the dressing to signal pressure changes to which the dressing and underlying wounds are subjected.

The preferred indicator for incorporating within the dressing are a series of temperature sensitive, color responsive encapsulated liquid crystals. Such encapsulated liquid crystals are commercially available in the form of a tape having a pressure sensitive adhesive coated on one side. Suitable tapes are commercially available. For example, those available from Seven C's Incorporated under their trademark E-Z Temp ®, from Davis Liquid Crystals, Inc. and from Eurand America, Inc. under their trademark Chameleon are suitable. These temperature sensing tapes have been applied directed to the forehead to measure temperature or have been applied to a flexible backing web for this purpose as shown by Flam in U.S. Pat. No. 3,661,142.

In the preferred embodiment of this invention as shown in the figures, the encapsulated temperature sensitive liquid crystals are employed as a tape having a plurality of boxes with accompanying indicia in form of numerals and/or letters. The tape 11 as shown in FIG. 1 consists of an array of 15 boxes where each box would represent the following temperature:

| Box | Temperature Legend (°C.) |
| --- | --- |
| 1 | 29° |
| 2 | 30° |
| 3 | 31° |
| 4 | 31.5° |
| 5 | 32 |
| 6 | 32.5 |
| 7 | 33 |
| 8 | 33.5 |
| 9 | 34 |
| A | 34.5 |
| B | 35 |
| C | 35.5 |
| D | 36 |
| E | 37 |
| M | 38 |

Of course, a tape can be employed with more or less than the 15 boxes shown and the rectangular boxes can be replaced by circles or other geometric patterns.

Figure 2:
FIG. 2 is a side view of the tape shown in FIG. 1 in enlarged detail.

The encapsulated temperature sensitive liquid crystal tape 11 as best shown in FIG. 2 consists of the liquid crystal substrate layer 25, a pressure sensitive acrylic type adhesive layer 24, an outer protective polymeric layer 26 of polyethylene terephthalate or other suitable material, and a release liner 23 such as silicone coated paper on the exposed surface of adhesive layer 24. Substrate layer 25 is visible through protective layer 26 as a black background with white indicia. When the temperature being sensed equals or is greater than the temperature range of one or more boxes, those boxes appear colored with green or blue green as the most prominent color. When the temperature being sensed is below that of a particular box, that box will not be visible against the black background. Similarly, when the temperature being sensed is substantially greater than the range of a particular box, that box will no longer be visible against the black background. Of course, other color schemes can be employed.

Figure 3:
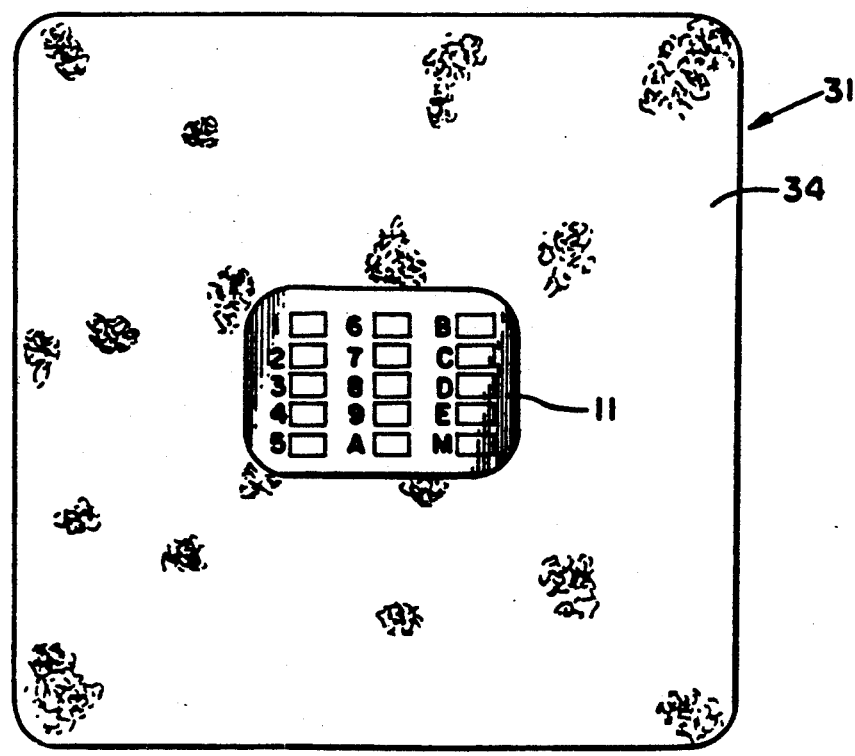
FIG. 3 is a top view of a dressing incorporating the tape shown in FIGS. 1 and 2 as an indicator means.
Figure 4:
FIG. 4 is a side view of the dressing of FIG. 3 in enlarged detail.
Figure 5:
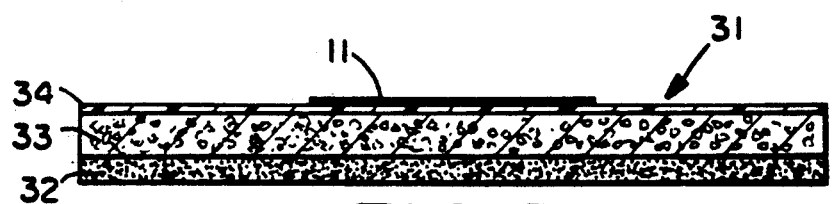
FIG. 5 is a side view similar to FIG. 4 of another dressing having an intermediate foam layer and also employing the tape shown in FIGS. 1 and 2 as an indicator means.

Tape 11 with release liner 23 removed is typically about 1 to 15 mils in thickness. Tape 11 is adhered by means of adhesive layer 24 to the top surface of a dressing. As shown in FIGS. 3 and 4, dressing 31 preferably consists of a fluid interactive hydrocolloid containing adhesive layer 32 and a backing film 34. As shown in FIG. 5, dressing 31 can include a layer of polymeric foam 33 between adhesive layer 32 and backing film 34. The surface of foam layer 33 which contacts fluid interactive hydrocolloid adhesive layer 32 can be coated with a pressure sensitive adhesive to increase the strength of the bond. Of course, the bottom of adhesive layer 32 would be covered with release paper prior to use.

Adhesive layer 32 is formulated by blending one or more water soluble or water swellable hydrocolloids with an elastomeric substance. Suitable hydrocolloids include sodium carboxymethylcellulose, pectin, gelatin, guar gum, locust bean gum, gum karaya, and mixtures thereof. Suitable elastomeric substances include polyisobutylene, mixtures of polyisobutylenes, or mixtures of one or more polyisobutylenes and one or more nonacrylic elastomers such as butyl rubber and styrene radial or block copolymers such as styrene-butadiene-styrene (S-B-S) and styrene-isoprene-styrene (S-I-S) block type copolymers. Other materials can be included within the fluid interactive hydrocolloid adhesive layer such as mineral oil, tackifiers, antioxidants, cohesive strengthening agents such as water-insoluble cross-linked sodium carboxymethylcellulose and water-insoluble cross-linked dextran, and pharmaceutically active materials such as antibiotics, antiseptics, antiinflammatory agents, or materials having wound healing or skin soothing properties.

The dressings shown in FIGS. 3 to 5 are suitable for use on intact skin which may be susceptible to decubitus ulcer formation or over already formed and exudating ulcers. For example, a 10 mil. thick version of the dressing shown in FIGS. 3 and 4 would be suitable for use in a prophylactic manner on a patient who does not exhibit signs of ulcer formation but who because of illness and/or lack of mobility is considered to be at risk. The indicator permits the health care professional to monitor the condition of the patient's skin. An increase in temperature noted, for example, by a shift from box number 4 to box number 9 or one of the letter boxes would signal that a change in treatment is needed. This could alert the health care professional to the need to increase blood circulation such as by massage, shifting the position of the patient more often, the use of a water-bed or other pressure distributing support system, or perhaps replacing the 10 mil. thick dressing with a thicker version such as 20 mil. or employing the more cushioned foam type dressing as shown in FIG. 5.

Monitoring changes in temperature beneath the dressing can also be useful in determining the stage of an underlying pressure sore. An increase in temperature is indicative of a shift from stage I (skin is red) to a stage II (skin is blistered) or stage III (skin is broken) condition. By being aware of such a shift, the health care professional is able to administer appropriate treatment.

Analogously, the indicator dressing of this invention can be employed to measure healing of a pressure sore. In this instance, the patient may be started with the thicker foam containing dressing of FIG. 5 and then by monitoring the healing the patient would be shifted to the thinner dressings of FIGS. 3 and 4.

Monitoring changes in temperature by means of the dressing and indicator device of this invention conveys other useful information such as the presence of infection associated with an increase in temperature or the presence of necrosis associated with a decrease in temperature. Again, the health care professional would be alerted to take appropriate medical procedures such as administering antibiotics if infection is confirmed or employing debriding agents to remove necrotic tissue. Other applications for the dressing and indicator device includes monitoring the hydration and/or dehydration level of the dressing and/or underlying wound since the temperature reading changes as a function of the thermal conductivity of the dressing.

Figure 6:
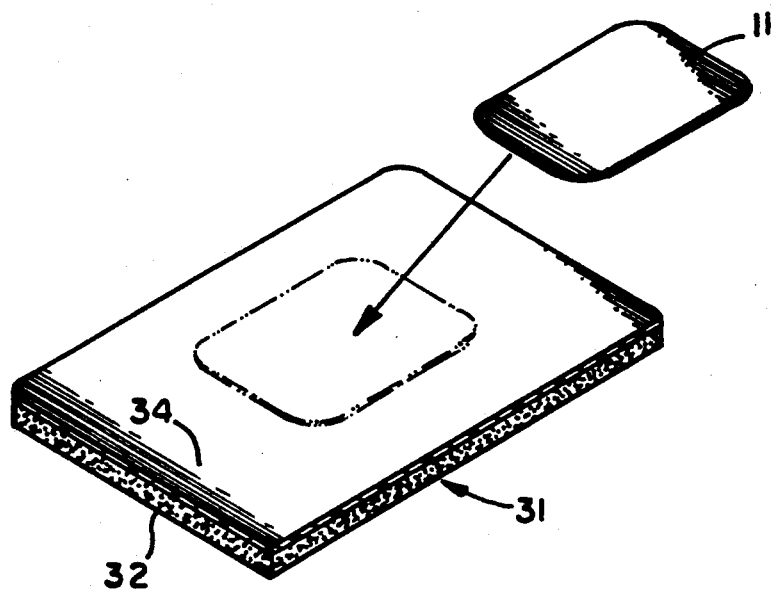
FIG. 6 is a perspective view showing the application of the temperature sensitive liquid crystal tape to a dressing which had been trimmed to fit onto the patient.

The indicator can be attached directly to the top surface of the dressing during the manufacturing step. Preferably, the dressing and indicator are packaged separately until use. This is a particularly desired case where the indicator measures temperature and the dressing is subjected to sterilization. As shown in FIG. 6, the health care professional is able to trim the dressing to the desired size and then remove release liner 23 from indicator tape 11 and adhere tape 11 to backing film 34 so as to be positioned directly over the area of the patient's body to be monitored.

The following examples are illustrative of the invention.

EXAMPLE 1

A wound dressing was prepared as follows:
An adhesive layer was prepared consisting of

| Ingredient | Weight Percent |
|---|---|
| Polyisobutylene (Vistanex ® LM-MH) | 8.0 |
| Butyl rubber (065) | 16.25 |
| Styrene-isoprene-styrene block copolymer (Kraton ® 1107) | 6.0 |
| Tackifier (Pentalyn ® H) | 12.75 |
| Mineral Oil | 11.5 |
| Pectin | 15.0 |
| Gelatin | 15.0 |
| Sodium carboxymethylcellulose | 15.0 |
| Antioxidant (Irganox ® 1010) | 0.5 |

The hydrocolloid containing adhesive composition of the above formula was compounded by first forming a preblend of the polyisobutylene, butyl rubber, styrene-isoprene-styrene block copolymer, and antioxidant in a Sigma blade kneader extruder while heating the mass at about 150°–155° C. The mineral oil was then added with continued agitation followed by the addition of the tackifier, temperature during this step was kept at about 120° C. Finally, the gelatin, pectin, and carboxymethylcellulose were added as powders while the mass was mixed and cooled. The resulting homogeneous mass was extruded to a thickness of about 10 mils. and a 1 mil. backing film of a polyether polyurethane was applied to one surface and a sheet of silicone coated release paper to the other surface.

The resulting dressing was die cut to a desired shape such as a 4 by 4 inch square, packaged, and sterilized.

A liquid crystal patch having a plurality of boxes capable of sensing temperatures from 29° C. to 38° C. coated with a layer of pressure sensitive adhesive was packaged in a carton with the sterilized dressing. Such liquid crystal patches are commercially available from Seven C's Incorporated.

Prior to use, the dressing is removed from the package and trimmed to the desired shape. Release liner 23 is removed and tape 11 is secured to dressing by pressing adhesive layer 24 onto backing film 34.

EXAMPLE 2

A wound dressing was prepared as described in Example 1 except the adhesive mass was extruded to a thickness of about 20 mils.

EXAMPLE 3

A temperature sensing wound dressing of the construction shown in FIG. 5 was prepared. The dressing includes a hydrocolloid containing adhesive mass of the formula described in Example 1 extruded to a thickness of about 50 mils. The foam layer employed was an open cell polyurethane foam, polyester type, of about 60 mils thickness having a polyurethane skin on one surface and a pressure sensitive acrylic adhesive on the other surface. The pressure sensitive acrylic adhesive was pressed into contact with the fluid interactive hydrocolloid containing adhesive layer. At the time of use, a liquid crystal temperature indicator was secured to the top surface of the wound dressing.

EXAMPLE 4

The following in vitro experiment was performed to compare temperature measurements on a heated surface measured through the dressing-type of Examples 1 to 3 with the temperature sensing tape applied directly to the surface.

A heated surface was covered with a ½ inch thick aluminium plate which in turn was covered with a 1 inch thick aluminium plate. Surface temperature of the top plate was measured with a calibrated Thermistor probe. Four samples of each of the dressings of Examples 1 to 3 with the liquid crystal tape applied to top surface were located across the 1 inch thick plate along with four samples of the liquid crystal tape applied directly by its adhesive layer 24.

The indicators were read and the corresponding temperatures were recorded. If one box was visible its corresponding temperature was recorded, if two boxes were visible then the average temperature was recorded.

The temperature of the aluminium plate was increased and after equilibration the indicators were again read. This was repeated until the maximum temperatures of the indicators was reached.

The following table lists the average of the temperature displayed by the four samples and includes the calculated standard deviation in parenthesis at each measurement.

| Temperature Measured With Probe (°F.) | Tape Applied Directly | Tape On Dressing of Example 1 | Tape On Dressing of Example 2 | Tape On Dressing of Example 3 |
|---|---|---|---|---|
| 83.9 | 84.4 (0) | 84.4 (0) | 84.4 (0) | |
| 85.6 | 85.2 (0) | 85.2 (0) | 85.2 (0) | 84.2 (0) |
| 86.2 | 86.0 (0) | 86.0 (0) | 86.0 (0) | 85.2 (0) |
| 87.4 | 88.0 (0) | 87.8 (0.4) | 87.8 (0.4) | 86.0 (0.9) |
| 88.7 | 89.2 (0.2) | 89.1 (0) | 89.1 (0) | 86.7 (0) |
| 90.0 | 89.8 (0) | 89.7 (0.2) | 89.7 (0.2) | 88.0 (0) |
| 91.1 | 91.6 (0) | 91.6 (0) | 91.6 (0) | 89.1 (0) |
| 93.0 | 92.4 (0) | 92.4 (0) | 92.4 (0) | 89.8 (0) |
| 95.5 | 95.6 (0.3) | 95.3 (0.1) | 95.2 (0) | 91.3 (0.6) |
| 96.5 | 96.0 (0) | 96.0 (0) | 96.0 (0) | 92.4 (0) |
| 97.6 | 97.1 (0.3) | 97.1 (0.3) | 97.1 (0.3) | 93.2 (0) |
| 98.9 | 97.5 (0) | 97.5 (0) | 97.5 (0) | 95.0 (0.2) |

-continued

| Temperature Measured With Probe (°F.) | Tape Applied Directly | Tape On Dressing of Example 1 | Tape On Dressing of Example 2 | Tape On Dressing of Example 3 |
| --- | --- | --- | --- | --- |
| 100.1 | 99.3 (0) | 99.3 (0) | 99.3 (0) | 95.5 (0) |
| 101.5 | 99.3 (0) | 99.3 (0) | 99.3 (0) | 96.0 (0.5) |
| 101.7 | | | | 96.6 (0.5) |

As will be seen, the readings made by the tape on top of the 10 mil and 20 mil dressing of Examples 1 and 2 were essentially identical to the readings made by the tape itself. The readings on top of the thicker dressing of Example 3 were offset in linear manner and still showed little standard derivation.

Thus, all three dressings with the indicator tape would convey in an accurate manner to the health care professional changes in temperature in the skin or a wound beneath each of the dressings.

What is claimed is:

1. The method of monitoring a patient to ascertain the susceptibility of the patient to formation of a decubitus ulcer which comprises
    a) covering that portion of the patient's body with a dressing having a skin contacting adhesive layer comprising one or more water soluble or swellable hydrocolloids dispersed in an elastomeric substance and a backing film layer,
    b) locating a temperature sensing liquid crystal tape having a plurality of indicators representative of different ranges of temperature onto the backing film of said dressing, and
    c) observing the indicators and noting changes in temperature over a period of time.

2. The method of monitoring a wound under a wound dressing to ascertain the rate of healing and presence of infection or necrosis without the need for removal of the dressing which comprises:
    a) covering the wound with a dressing having a skin contacting adhesive layer comprising one or more water soluble or swellable hydrocolloids dispersed in an elastomeric substance and a backing film layer,
    b) locating a temperature sensing liquid crystal tape having a plurality of indicators representative of different ranges of temperature onto the backing film of said dressing, and
    (c) observing the indicators and noting changes in temperature over a period of time.

3. The method of monitoring the degree of hydration of a wound under a wound dressing or the degree of hydration of the wound dressing itself without the need for removal of the dressing which comprises:
    a) covering the wound with a dressing having a skin contacting adhesive layer comprising one or more water soluble or swellable hydrocolloids dispersed in an elastomeric substance and a backing film layer,
    b) locating a temperature sensing liquid crystal tape having a plurality of indicators representative of different ranges of temperature onto the backing film of said dressing, and
    c) observing the indicators and noting changes in temperature over a period of time.

* * * * *